United States Patent [19]

Gosalvez

[11] 4,138,480

[45] Feb. 6, 1979

[54] NOVEL ANTHRACYCLINE GLYCOSIDES AND METHODS OF PREPARING THE SAME

[76] Inventor: Mario G. Gosalvez, C/Caleruega 21,7°A, Pinar de Chamartin Madrid 33, Spain

[21] Appl. No.: 758,446

[22] Filed: Jan. 11, 1977

[30] Foreign Application Priority Data

Jan. 16, 1976 [ES] Spain ................................. 444.380

[51] Int. Cl.² ....................... A61K 31/71; C07H 15/24
[52] U.S. Cl. ......................................... 424/180; 536/4; 536/17; 536/121
[58] Field of Search ........................... 536/4, 17, 121; 424/180

[56] References Cited

U.S. PATENT DOCUMENTS

| | | | |
|---|---|---|---|
| 3,074,927 | 1/1963 | Saltman et al. | 536/121 |
| 3,590,028 | 6/1971 | Arcamone et al. | 536/17 |
| 4,024,224 | 5/1977 | Arcamone et al. | 536/4 |

Primary Examiner—Johnnie R. Brown
Attorney, Agent, or Firm—Holman & Stern

[57] ABSTRACT

Metallic derivatives of anthracycline glycosides such as doxorubicin and daunorubicin are prepared by admixing divalent or trivalent metal cations, preferably Fe(III), with the glycoside and adjusting pH to promote chelation of the metal by bidentate ligands of the glycoside. The derivatives are isolated in essentially monomeric form, and preferably lyophilized for later reconstitution immediately before use in the treatment of transplanted tumors in mice. As compared with the parent glycosides, the derivatives exhibit greatly diminished cardiotoxicity and less general, hematological and digestive toxicity as well. At the same time, the antineoplastic efficacy of the derivatives in transplanted mouse tumor test systems appears to be approximately equivalent to that of the parent glycoside on a mg. to mg. basis. As a result, the therapeutic index of the derivative is greatly elevated over that of the parent, since the derivative may be safely administered in greater quantities.

10 Claims, 3 Drawing Figures

NOVEL ANTHRACYCLINE GLYCOSIDES AND METHODS OF PREPARING THE SAME

The invention described herein was made in the course of or under a contract with the United States Department of Health, Education and Welfare.

BACKGROUND OF THE INVENTION

The anthracycline glycoside antibiotics are those in which a tetrahydronaphthacene chromophore is linked to a sugar, most commonly a basic sugar. As representative of such antibiotics may be mentioned the following:

| | |
|---|---|
| doxorubicin | reticulomycin B |
| daunorubicin | isoquinocycline A |
| daunorubicinol | galirubin |
| pyrromycin | mycetin |
| rutilantin | mycetin A |
| cinerubin A | violacin |
| cinerubin B | α-citromycin |
| aklavin | γ-citromycin |
| rhodomycin A | 10-deoxyrhodomycin |
| rhodomycin B | β-isorhodomycin |
| γ-rhodomycin 1 | γ-isorhodomycin |
| γ-rhodomycin 2 | ε-isorhodomycin |
| γ-rhodomycin 3 | minomycin |
| γ-rhodomycin 4 | aquayamycin |
| isorhodomycin A | ayamycin |
| reticulomycin A | nogalomycin |
| doxorubicinol | |

Of these, doxorubicin (U.S. Pat. No. 3,590,028), daunorubicin (G.B. Pat. No. 1,003,383), and their derivatives and other analogs have gained wide attention as oncolytic agents, i.e., agents useful in the treatment of leukemia and in other cancer chemotherapy. In the formulas shown below and in the accompanying drawing, the structure of doxorubicin appears from Formula I (FIG. 1 of the drawing) wherein $R_1$ is —COCH$_2$OH and R is the particular daunosaminil moiety depicted in Formula II (FIG. 2 of the drawing). When, instead, $R_1$ is —COCH$_3$, the structure of daunorubicin results.

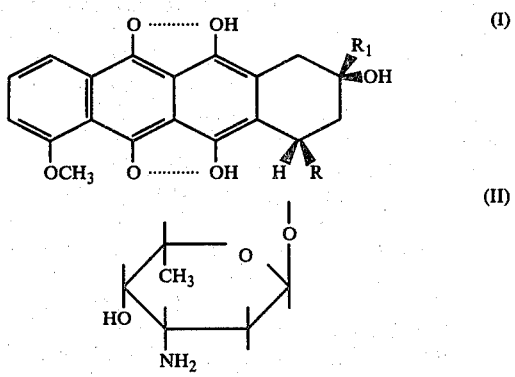

Many analogs of these compounds have been prepared, principally by operations on the hydroxymethyl ketone moiety of doxorubicin, the methyl ketone moiety of daunorubicin, and on the daunosaminil amino group of both compounds. Representative analogs are described in, e.g., U.S. Pat. No. 3,686,136; K. Yamamoto et al., *J. Med. Chem.*, 15, 872 (1973); German Pat. Nos. 2,327,211; 2,557,537; and 1,920,198; E. Bachman et al., *Agents and Actions* 5/4, 383 (1975); P. Chandra, *Cancer Chemother. Rep.* 6, 115 (1975); F. Arcamone et al., id. at 123; and G. Zbinden et al., *Cancer Chemother. Rep.* 4, 707 (1975), the disclosures of which are incorporated herein by reference. As one derivative of especial interest may be mentioned rubidazone, i.e., the compound of Formula I wherein R is as in Formula II and $R_1$ is —CCH$_3$NNHCO—C$_6$H$_5$. Others are doxorubicinol and daunorubicinol.

One problem that has persistently attended the use of these oncolytic anthracycline glycosides arises from their high general, hematological, digestive and cardiac toxicity, which has restricted their more extensive use at doses adequate for effective cancer chemotherapy. The cardiotoxicity of these drugs has proven especially troublesome. Thus, severe cardiotoxicity, oftentimes lethal, attends the use of doxorubicin at cumulative doses in excess of 500 mg. per square meter. The problem of toxicity associated with doxorubicin doubtless has inspired the many attempts to modify the compound along useful lines, but as recently as 1975 one group of investigators was forced to conclude that "the compound which combines the strong and broad-spectrum antitumor activity of adriamycin [doxorubicin] with very low cardiac toxicity has not yet been identified." G. Zbinden et al., *Cancer Chemother. Rep.* 59, 707.

In the course of examining the cardiotoxicity of doxorubicin, I discovered it to be a potent inhibitor of the Na and K dependent cardiac membrane transport ATPase, and hence an inhibitor of K transport. I also observed that this inhibition was counteracted by calcium, suggesting that doxorubicin forms a complex with calcium. The cumulative cardiotoxicity of doxorubicin would be explained if the calcium-doxorubicin complex formed in blood was inactive in the ATPase while the small proportion of free glycoside bound essentially irreversibly to the enzyme. I concluded that tight monomeric metallic saturated derivatives of the anthracycline glcosides, such as derivatives embodying metal cations whose affinity for the polydentate ligands of the glycoside was greater than that of calcium, would be non-cardiotoxic. At the same time, the resulting modification might be insufficient to affect the mechanism of the drug's oncolytic activity, which may involve intercalation in the DNA of tumor cells. Whatever the mechanism of action, and I do not wish to be bound by any particular theory of efficacy, I have now prepared metal derivatives of anthracycline glycosides which, while retaining the anti-tumor efficacy of the parent compounds against transplanted tumors in mice, appear essentially to eliminate their characteristic cardiotoxicity. The new compounds present other significant advantages as well, as is reported hereinafter.

Some workers have reported complexes of metals with anthracycline glycosides. For example, D. W. Yesair et al., in *A.A.C.R. Abstr.* 285 (1974), reported that adriamycin [doxorubicin] and daunomycin [daunorubicin] complex with Fe(II), Co(II), Cu(II) and other metal cations. These workers combined Cu(II) and both adriamycin ("A") and daunomycin ("D"), reporting mole ratios for the latter of Cu(II):D (1:1), and concluded that "cuprous ions protect somewhat against delayed anthracycline toxicity." Subsequently, other investigators who attempted to confirm this work found that a 1:2:Cu(II):D polymer complex results from the Yesair method (50% of the metal cation remaining uncomplexed) but that, in vivo, "complete dissociation of the complex occurs immediately." K. Mailer et al., *Biochem. Pharm.* 25, 2085 (1976). These investigators concluded that effects previously observed in vivo "cannot be due to the presence of the chelate form of these drugs."

The metal derivatives of the anthracycline glycosides prepared according to the present invention are in essentially monomeric form (i.e., one glycoside per molecule of derivative), and undue polymerization which may, for example, prevent intercalation in the DNA of tumor cells, is essentially avoided by novel methods which discourage the active presence of free metal. At the same time, the compositions of this invention preferably include plural metal cations per molecule of anthracycline glycoside.

BRIEF SUMMARY OF THE INVENTION

The method of this invention involves the combination in solution of an anthracycline glycoside having at least one bidentate ligand and a divalent or trivalent metal cation whose affinity for the ligand is greater than that of Ca(II); adjusting the pH of the resulting system to promote chelation of metal by the bidentate ligands; separating the resulting solution from any solid metal-containing byproduct; and promptly treating the resulting solution to halt further reaction between glycoside and metal cations. In the separation step, a substantial amount of macromolecular polyglycosidic byproduct may also be eliminated. Novel compounds prepared by the foregoing method have proven to be essentially free of cardiotoxicity, yet retain oncolytic activity against transplanted tumors in mice exhibited by the parent glycoside, on an essentially mg. to mg. comparative basis. Introduction of metal in the glycosides changes the visible, ultraviolet, infrared and nuclear magnetic resonance spectra of the parent compounds, thus indicating a change in the molecular structure of the antibiotics due to the partial nature of covalent bonding resulting from interaction with the metal cations. The metal also appears to diminish catabolism of the parent compound into toxic derivatives.

As compared with parent oncolytic compounds, the metal derivatives of this invention exhibit significantly reduced general, digestive and hematological toxicity. The introduction of metal alters the electronic properties of the parent compound, and thus appears to profoundly affect its permeability properties. Thus, the preferred compound of the invention, triferric doxorubicin, appears capable of passing both hematoencephalic and intestinal barriers, whereas doxorubicin itself does not to an effective degree. Such properties may be expected to be manifested in remaining embodiments of the invention as well, so that compounds of this invention may be administered orally, as in enteric-coated form. In addition to all of the foregoing, introduction of metal cations appears to significantly diminish immunosuppressive properties of the corresponding parent compound. Thus, for example, in comparative testing doxorubicin depressed spleen weight and immunocompetent cells to a significant extent, while triferric doxorubicin prepared according to this invention proved much less immunosuppressive. Finally, when compounds prepared according to this invention are parenterally administered, the necrosis adjacent the site of administration which attends use of the corresponding parent, e.g., doxorubicin, is apparently eliminated. The seemingly greater specificity of the metal derivatives of this invention may be attributable to altered permeability properties, as mentioned above. Whatever the mechanism of advantage, it should be apparent that the compounds provided by the invention exhibit a broad spectrum of beneficial properties not present in the corresponding parent compounds.

DETAILED DESCRIPTION OF THE INVENTION

Figure 1:
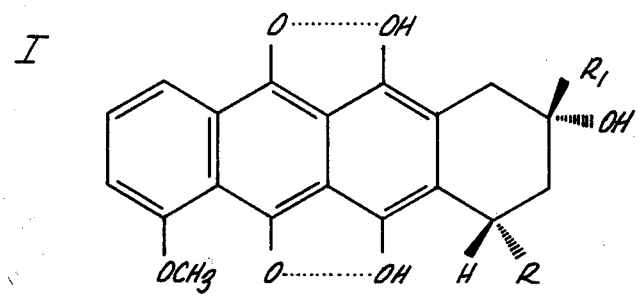
Figure 2:
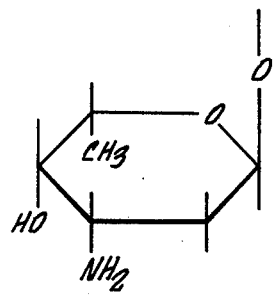
Figure 3:
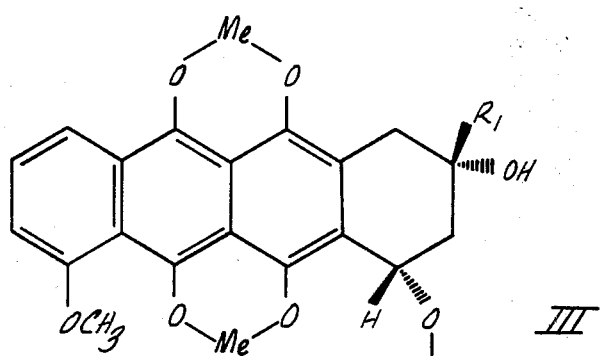

Preferred embodiments of the invention may be conveniently discussed by reference to Formula III, shown below and in FIG. 3 of the accompanying drawing, which depicts the structure, as presently understood, of certain trimetallic anthracycline glycosides made available by the invention.

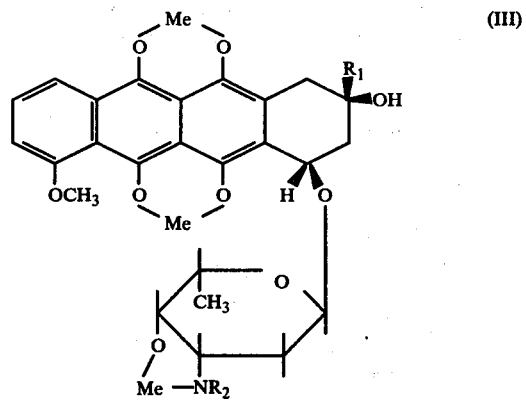

In Formula III, when $R_2$ is hydrogen and $R_1$ is —$COCH_3$ or —$COCH_2OH$, respectively, trimetallic daunorubicin and trimetallic doxorubicin result. As will be apparent to those skilled in the art, $R_1$ may be otherwise derivatized and $R_2$ may, for example, embody an acyl or other group, in keeping with the analogs previously discussed. In any event, it will be seen that the bidentate ligands of the parent compound are, in the preferred case, all occupied by metal ("Me"). When in forming the compounds of the invention less metal reactant is employed than is required essentially to satisfy all bidentate ligands of the parent glycoside, it will be appreciated that in the resulting composition the metal cation may be distributed in various ways among the ligands of individual glycosides making up the composition. In such cases, the ligands of the aglycone are believed to predominate in competition for metal cation. Most preferably, however, in forming the compounds of the invention at least about n moles of metal cation are supplied per mole of glycoside, n being the number of bidentate ligands in the glycoside molecule. Indeed, a stoichiometric excess of metal cation may be employed, subject to the precautions described below. Preferably in the case of glycosides having three bidentate ligands per molecule, resulting compositions contain at least about 2 moles of metal per mole of glycoside. Most preferably in this case, the ratio is about 3:1, metal to glycoside. While, as before stated, I do not wish to be bound by theory, it is possible that the unoccupied bidentate ligands of the parent glycosides act as binding sites for inhibition of the Na-K ATPase, so that attention is desirably paid to ensuring their occupation by metal.

In the case illustrated in the drawing, the bidentate ligands of the anthracylinone (aglycone) are dicarbonyl. A different ligand appears in the daunosaminil moiety, arising from the adjacency of an amino group and a glycosyl hydroxyl group. Of course, particular anthracycline glycosides advantaged by the practice of this invention may have other varieties of complexing ligands. A variety of other bidentate ligands are described in J. Kleinberg et al., *Inorganic Chemistry*, pp. 218–20, D.C. Heath & Co., Boston (1960), the disclosure of which is incorporated herein by reference.

The compounds of the invention are formed in solution, preferably aqueous, by the combination of the parent glycoside and metal cation supplied in any convenient form, preferably as a salt. Cations employed are those whose affinity for the ligand is greater than that of Ca(II), as determined by Hill's method, e.g., divalent cations such as Mn(II), Cd(II), Fe(II), Zn(II), Co(II), Pb(II), Ni(II), Cu(II) and Hg(II), and trivalent cations such as Fe(III) and Al(III). Preferred cations include Fe(II), Fe(III), Cu(II) and Co(II), Fe(III) being most preferred. Preferred metal salt reactants include chlorides, sulfates and nitrates, although hydroxides may also serve.

Ordinarily, when the metal reactant and glycoside are first combined in aqueous solution the resulting system is relatively acidic. While solution of the metal reactant is facilitated at acid pH, I prefer next to adjust pH to near neutrality to deprotonate the bidentate ligands and favor chelation of the cations. Thus, the reaction system is desirably adjusted in pH to an extent sufficient to favor chelation, preferably to near neutrality, e.g., pH from about 6.5 to about 7.5, most preferably from about 6.8 to about 7.2. Adjustment of pH should be gradual to minimize precipitation of solid metal compound whose presence, I believe, tends toward formation of inefficacious polyglycoside-containing moieties.

The temperature of the reaction is controlled by solubility considerations (low limit) and the degradation temperature of the particular anthracycline involved (high limit). Ordinarily during pH adjustment temperature is maintained within the range from about 15° to about 50° C.

Following pH adjustment the resulting generally monomeric metal-containing derivatives are desirably promptly separated from any solid, metal-containing byproducts, as by filtration. A majority of the glycosidic moieties contained in the filtrate are monomeric in form. As revealed by ultrafiltration techniques, in preferred embodiments of the invention more than about 95% and optimally more than about 99% of the filtrate's glycosidic content is monomeric. The resulting solution, which invariably contains a modicum of uncomplexed soluble metal cations, is then promptly treated to halt further metal-glycoside reaction which might tend toward creation of inefficacious polyglycoside-containing materials like those believed to have characterized prior art compositions such as those reported by Yesair, supra. Free metal might be absorbed by, e.g., magnesium carbonate or removed by chromatographic means. Most preferably, after optional dosification, the filtered solution is simply, and promptly, solidified by rapid freezing. By promptly freezing the filtered reaction mixture in this fashion, further metal-glycoside reaction which might otherwise occur is effectively halted. Thereafter, the product is preferably lyophilized and stored at low humidity, most preferably less than about 1%.

The lyophilized material, which ordinarily will include a major proportion of mannitol or other excipient, should be used parenterally essentially immediately following reconstitution with a pharmaceutically acceptable carrier, e.g., sterile water to a final concentration of, e.g., 1 ml/2.5 mg. multimetallic anthracycline glycoside. Alternatively, compounds such as, e.g., triferric doxorubicin may be administered orally, in enteric-coated dosage form.

While the preferred method of preparing the anthracycline glycoside-metal in accordance with the present invention is as described above, i.e, reacting the preformed anthracycline glycoside, e.g., doxorubicin or daunorubicin, with the appropriate metal salt reactant, it will be understood that it may also be possible to effect metal chelation as one of the final steps in an anthracycline glycoside synthesis procedure, without actually isolating the free anthracycline glycoside as such.

Other candidates for use in this invention are anthracycline glycosides in which the glycoside moiety differs from that normally joined to a given anthracyclinone (aglycone) as it is elaborated by a Streptomycetes, in the form of a glycoside. Such anthracycline glycosides are prepared by reacting an appropriate anthracyclinone, e.g., daunorubicinone, with an appropriate alkylating agent as is described by Penco, *Chim. Ind.* (Milan), 50, 908 (1968); *C. A.* 70, 1953j; French Pat. No. 2,183,710. Suitable alkylating agents are 2,3,4,6-tri-O-acetyl-α-D-glucopyranosyl bromide; 3,4,6-tri-O-acetyl-2-deoxy-2-trifluoroacetamido-α-D-glucopyranosyl bromide; di-(N-trifluoroactyl-α-daunosamine).

By such reactions, the aglycones of the herein named anthracycline glycosides can be converted to a wide variety of different anthracycline glycosides. The daunosamine moieties of daunorubicin and doxorubicin can be replaced by, for example, rhodosamine, or other basic sugars.

The metal chelates described herein may also prove useful for the control of trace metal ions, especially as regards their ability to serve as sources of trace metals for purposes such as plant growth. The metal chelates of $Fe^{+3}$ might prove of special value for use in the treatment of iron chlorosis, or deficiency, in plants. The amount of ferric chelate used would be determined by the content of available iron in the particular soil in which the plants are growing. The amount of ferric chelate used desirably should be sufficient to eliminate the chlorotic condition within a period of one to two weeks. Additionally, the compounds might also serve as stabilizers for various systems, such as plastics derived from vinylidene chloride, wherein traces of chloride give rise to instability of the plastic. In such systems the metal chelate would desirably be used at concentrations sufficient to overcome the effects of the maximum amount of chloride which could be released.

The following examples are provided as an illustration and they do not impose limitations on the invention because a number of other examples are possible on the same basis and within the application on the spirit of this invention.

BIOCHEMICAL AND PHARMACOLOGICAL STUDY OF PRODUCTS OF THIS INVENTION

In Table I below, the dissociation constants of doxorubicin and daunorubicin with different metals are presented. The metals are listed in the order of their general affinity of chelation. The constant has been defined for some of them. As shown, the metal with the highest affinity for doxorubicin and daunorubicin is ferric iron and the metal with the least affinity is calcium. The dissociation constant was calculated by Hill's method, taking advantage of the change in color upon the formation of the metallic derivatives of the antibiotics. The dissociation constant reported is that for the strongest ligand-metal interaction in each case. As used hereafter, reference to the affinity of a metal for any given glycoside's polydentate "ligand" relates, in the case of a glycoside having plural ligands, to that which presents the strongest ligand-metal interaction, as determined by the Hill plotting method.

TABLE I

| Metal | Dissociation Constant of the Metallic Derivative with Doxorubicin and Daunorubicin |
|---|---|
| Fe (III) | $5 \times 10^{-7}$ M |
| Hg (II) | --- |
| Cu (II) | $1 \times 10^{-6}$ M |
| Al (III) | --- |
| Ni (II) | --- |
| Pb (II) | --- |
| Co (II) | $1.3 \times 10^{-5}$ M |
| Zn (II) | --- |
| Fe (II) | $3.5 \times 10^{-5}$ M |
| Cd (II) | --- |
| Mn (II) | --- |
| Ca (II) | $12.7 \times 10^{-5}$ M |
| Mg (II) | --- |

The experiment of Table I shows that the metals with the highest affinity for doxorubicin and daunorubicin are $Fe^{3+}$, $Cu^{2+}$ and $Co^{2+}$, with $Ca^{2+}$ having the least affinity. The rest of the metals must have an intermediate affinity, according to their position in the table.

In Table II, the effect of doxorubicin, ferric-doxorubicin 2:1 and ferric doxorubicin 3:1, on the activity of the ATPase sodiumpotassium dependent enzyme, isolated from rabbit heart, is illustrated.

TABLE II

Percent of the ATPase Na-K Dependent Acitivity in the Presence of Increasing Concentrations of Anthracyclines

| Drug | OM | $10^{-13}$ M | $10^{-11}$ M | $10^{-9}$ M | $10^{-7}$ M | $10^{-5}$ M |
|---|---|---|---|---|---|---|
| Doxorubicin | 100% | 65% | 40% | 25% | 25% | 25% |
| Ferric-Doxorubicin 1:1 | 100% | 80% | 60% | 60% | 60% | 60% |
| Ferric-Doxorubicin 2:1 | 100% | 100% | 100% | 100% | 100% | 100% |
| Ferric-Doxorubican 3:1 | 100% | 100% | 100% | 100% | 100% | 100% |

The experiment of Table II shows that doxorubicin is a strong inhibitor of the Na-K ATPase, which now appears to be intimately related to cardiotoxicity. Nevertheless, the 2:1 and 3:1 ferric derivatives of doxorubicin are completely inactive in the enzyme, while the ferric derivative 1:1 of doxorubicin is partially inhibiting. From these facts, it can be deduced, on the basis of the results of Table I as well, that the metallic derivative of doxorubicin formed with the metal proportion 2:1 or higher, lacks the inhibiting effect on the Na-K ATPase, that is to say, they would lack cardiotoxicity. Similar work has shown that metallic derivatives of daunorubicin likewise do not inhibit the Na-K AtPase. The remaining chelates described herein may be expected to behave similarly. For example, the following doxorubicin analogs have been shown to inhibit Na-K ATPase. Their corresponding metal derivatives, when prepared as previously described for the case of doxorubicin, may be expected to exhibit marked reduction in cardiotoxicity. The compounds have the structure depicted in Formula I wherein R is as in Formula II and $R_1$ is as given.

TABLE III

| ANALOGS | $R_1$ | Concentration for 50% Inhibition Na—K ATPase |
|---|---|---|
| RUBIDAZONE | $-C(CH_3)=N-NHCO-C_6H_5$ | $10^{-11}$ M |
| NSC-219977 | $-C(CH_3)=N-NH-CO-C_6H_4Cl$ | $10^{-11}$ M |
| NSC-221264 | $-C(CH_3)=N-NH-CO-C_6H_4OH$ | $10^{-10}$ M |
| NSC-227013 | $-C(CH_3)=N-NH-CO-C_6H_4-N(CH_3)_2$ | $10^{-10}$ M |
| NSC-219976 | $-C(CH_3)=N-NH-CO-C_6H_4OCH_3$ | $10^{-9}$ M |
| NSC-237638 | $-C(=O)-O-CH_3$ | $10^{-9}$ M |
| NSC-236672 | $-C(CH_3)=N-NH-CO-C_6H_4\,pH$ | $10^{-9}$ M |
| NSC-234740 | $-C(CH_3)=N-NH-CO-CH_6H_4O-(CH_2)_7CH_3$ | $10^{-8}$ M |
| NSC-233854 | $-C(CH_3)=N-NH-CO-C_6H_4-Li$ | $10^{-7}$ M |

TABLE III-continued

| ANALOGS | $R_1$ | Concentration for 50% Inhibition Na—K ATPase |
|---|---|---|
| NSC-211391 | $-\underset{\underset{CH_3}{\mid}}{C}=N-NH-CO-(CH_2)_3-CH_3$ | $10^{-6}$ M |
| NSC-221266 | $-\underset{\underset{CH_3}{\mid}}{C}=N-NH-CO-C_6H_4-Cl$ | $10^{-6}$ M |
| NSC-237672 | $-\underset{\underset{CH_3}{\mid}}{C}=N-NH-CO-C_6H_4-Cl$ | $10^{-5}$ M |
| NSC-216071 | $-\underset{\underset{CH_2OH}{\mid}}{C}=N-NH-CO-C_6H_5$ | $10^{-5}$ M |
| NSC-221265 | $-\underset{\underset{CH_3}{\mid}}{C}=N-NH-CO-C_6H_4-NO_2$ | $10^{-5}$ M |

Table IV illustrates the comparison between doxorubicin and ferric-doxorubicin 2.5:1 on the DNA synthesis of leukemia 1210 mouse cells.

TABLE IV

Percent of Inhibition of DNA Synthesis at Increasing Concentrations of Anthracycline

| Drug | 0 μM | 3 μM | 5 μM | 7.5 μM | 10 μM |
|---|---|---|---|---|---|
| Doxorubicin | 0% | 60% | 68% | 75% | 90% |
| Ferric-Doxorubicin (2.5:1) | 0% | 50% | 70% | 80% | 90% |

The experiment of Table IV shows that the ferric derivatives have the same inhibiting effect on DNA synthesis as the parent antibiotic and therefore that the antitumoral activity, which is based on the inhibition of DNA synthesis, remains in the metal derivative.

In Table V, the toxicity of doxorubicin and ferricdoxorubicin is compared. This experiment was carried out with samples of ferric-doxorubicin produced with various proportions of iron greater than 2:1 with respect to the antibiotic, and each sample led to similar results. The drugs were administered by only one intraperitoneal injection to groups of ten mice and the numbers of survivors were recorded after eight days.

TABLE V

Percent of Surviving Mice After the Administration of Anthracyclines

| Drug | Doses: 10 mg/kg | 20 mg/kg | 30 mg/kg | 40 mg/kg | 50 mg/kg | 60 mg/kg |
|---|---|---|---|---|---|---|
| Doxorubicin | 100% | 60% | 0% | 0% | 0% | 0% |
| Ferric-Doxorubicin | 100% | 100% | 100% | 70% | 40% | 30% |

This experiment shows that ferric-doxorubicin is much less toxic than doxorubicin. Upon graphically presenting the data of Table V, it is calculated that the mean lethal dose of the ferric doxorubicin employed is 47 mg./kg.

Table VI shows the therapeutic activity of ferric-doxorubicin in leukemia P-338 of the mouse. In this experiment, ferric-doxorubicin produced with various proportions of metal to antibiotic greater than and including the proportion 2:1 were used, and with all of them, similar results were obtained. The mean survival rate was measured of a group of ten mice inoculated with 100,000 leukemic cells and treated the first day after inoculation with increasing doses of doxorubicin and ferric-doxorubicin.

TABLE VI

Days of Mean Survival of Leukemic Mice

| Drug | Dose (i.p.): 0 mg/kg | 4 mg/kg | 8 mg/kg | 12 mg/kg | 24 mg/kg | 36 mg/kg |
|---|---|---|---|---|---|---|
| Doxorubicin | 11 days | 50 days | 48 days | 42 days | 6 days | 4 days |
| Ferric Doxorubicin | 11 days | 50 days | 48 days | 42 days | 35 days | 23 days |

The experiment of Table VI shows that ferric-doxorubicin has a therapeutic equal to that of doxorubicin in the leukemic mouse but that it can be used at greater doses, due to its low toxicity.

In Table VII, the electrocardiographic alterations immediately following the intravenous injection to the rabbit of increasing doses of doxorubicin and ferric-doxorubicin 3:1 are illustrated.

This experiment shows that there are no significant alterations of the electrocardiogram with ferric-doxorubicin while they are very intense with doxorubicin, and it corroborates the lack of cardiotoxicity of ferric-doxorubicin.

TABLE VII

Electrocardiographic Alterations

| Drug | Dose: 5 mg/kg | 10 mg/kg | 15 mg/kg | 20 mg/kg | 30 mg/kg |
|---|---|---|---|---|---|
| Doxorubicin | leveled T wave | Neg. T-wave | Neg. T wide QRS | Neg. T wide QRS Arrhythmia | Neg. T wide QRS Bradycardiac Arrhythmia |
| Ferric-Doxorubicin | | None | None | Without significant alteration. | Without significant alteration. |

Table VIII shows the visible and infrared spectral characteristics of doxorubicin and ferric-doxorubicin (3:1).

TABLE VIII

| Wavelength | Optical absorption or percent of transmittance at different wavelengths | | | | | | | |
|---|---|---|---|---|---|---|---|---|
| | 1730 cm$^{-1}$ | 1620 cm$^{-1}$ | 1590 cm$^{-1}$ | 1585 cm$^{-1}$ | 1570 cm$^{-1}$ | 600 nm | 480 nm | 280 nm |
| Doxorubicin | 30% | 50% | 0% | 30% | 0% | 0% | 0.180 | 0.200 |
| Ferric-Doxorubicin | 10% | 23% | 20% | 0% | 37% | 0.080 | 0.100 | 0.360 |

From Table VIII it can be observed that the complexes show different absorptions from the free compounds at different wavelengths and that also, the complexes have different peaks of absorption.

Table IX shows a comparison between the hematological toxicity of doxorubicin and ferric-doxorubicin (3:1).

TABLE IX

Hematological Toxicity of Anthracycline Derivatives (Leucocyte Count/mm$^3$)

| Drug | Dose | Day 0 | Day 7 |
|---|---|---|---|
| Doxorubicin | 10 mg/kg | 4.700 | 3.300 |
| | 20 mg/kg | 4.700 | 2.400 |
| Ferric-Doxorubicin | 10 mg/kg | 4.700 | 5.100 |
| | 15 mg/kg | 4.700 | 4.400 |
| | 20 mg/kg | 4.700 | 4.400 |
| | 30 mg/kg | 4.700 | 3.600 |
| | 40 mg/kg | 4.700 | 3.800 |
| | 50 mg/kg | 4.700 | 2.800 |
| | 60 mg/kg | 4.700 | 1.800 |

It can be observed that the hematological toxicity observed with 20 mg/kg of doxorubicin is not reached with ferric-doxorubicin until concentrations greater than 50 mg/kg.

The biochemical and pharmacological study that has been presented in Tables I–IX show, in summary, that doxorubicin and daunorubicin form metal chelate derivatives with all the metals listed in Table I; that these metal chelate derivatives are especially stable when formed with ferric iron, copper and cobalt; and that the metal chelate derivatives formed with a metal to antibiotic ratio of 2:1 or greater are inactive in the ATPase Na-K dependent enzyme, less toxic in the mouse and rabbit and therapeutically active in mouse leukemia. Although the majority of the experiments which are shown here have been carried out with ferric-doxorubicin with different proportions of metal to antibiotic (2:1 or greater), the results are similar with metal chelate derivatives of both antibiotics with various metals made in various proportions.

EXAMPLE 1

Ferric-Doxorubicin 3:1 (Triferric Doxorubicin)

One hundred micromoles of doxorubicin and three hundred micromoles of ferric chloride are mixed in aqueous solution at room temperature, under continuous stirring in a flask provided with a recording pH meter. Upon contact of the iron with the antibiotic, the complex begins to form and the pH is adjusted slowly to pH 7.3 with concentrated NaOH. Then the solution is adjusted with water to a concentration of 1 mg. of doxorubicin per ml. and a tris-hydroxymethyl aminomethance buffer at pH 7.3 is added to a final concentration of 12 mM. Immediately, the solution is quickly passed through a 0.22 micron pore sterile filter. Then the solution is immediately poured into a small flask, frozen by immersion in liquid nitrogen and lyophilized. The lyophilized powder is sterilely sealed in vials containing 10 mg. which are to be reconstituted immediately prior to use with 10 ml. of water.

In like manner, other anthracycline glycosides may be reacted with ferric chloride to produce corresponding ferric chelates.

EXAMPLE 2

Ferric-Doxorubicin (3.5:1)

The procedure of Example 1 is followed but using 350 micromoles of ferric chloride and a reaction temperature of 42° C.

EXAMPLE 3

Ferric-Doxorubicin (2.5:1)

The procedure of Example 1 is followed but using 250 micromoles of ferric chloride and adjusting the pH to 6.9.

EXAMPLE 4

Ferric-Doxorubicin (2:1)

The procedure of Example 3 is repeated by using 200 micromoles of ferric chloride to afford the 2:1 metallic derivative.

EXAMPLE 5

Ferric-Doxorubicin (1:1)

The procedure of Example 1 is followed but using 100 micromoles of ferric hydroxide.

EXAMPLE 6

Cupric-Doxorubicin

The procedure of Example 1 is followed but using cupric sulphate instead of ferric chloride.

EXAMPLE 7

Cobalt-Doxorubicin

The procedure of Example 1 is followed but using cobalt chloride instead of ferric chloride.

In light of the foregoing, other expedients by which compounds of this invention may be obtained will occur to the art-skilled. For example, the monochlorohydrate of daunorubicin may be substituted for doxorubicin in any of the foregoing procedures. Again, polar solvents other than water may be employed, e.g., the metal derivatives may be formed by combining cation and glycoside in alcohol, accompanied by stirring and the exclusion of air. Likewise numerous metal-containing reactants other than $FeCl_3$ may be employed. For example:

Table X

| Representative Metal-Containing Salts Useful in the Invention | |
|---|---|
| $FeSO_4$ | $HgCl_2$ |
| $CuSO_4$ | $ZnSO_4$ |

Table X-continued

| Representative Metal-Containing Salts Useful in the Invention | |
|---|---|
| NiCl$_2$ | Cd(NO$_3$)$_2$ |
| CoCl$_2$ | Pb(OCOCH$_3$)$_2$ |
| Al$_2$(SO$_4$)$_3$ | Pb(NO$_3$)$_2$ |

What is claimed is:

1. A method which comprises:
   (1) combining in solution an anthracycline glycoside whose aglycone moiety has at least one bidentate ligand and a divalent or trivalent metal cation whose affinity for the ligand is greater than that of Ca(II);
   (2) gradually increasing the pH of the resulting system to within the pH range of from about 6.5 to about 7.5 to promote chelation of metal cation by bidentate ligands, said chelation predominating at said aglycone moiety, thereby forming soluble monomeric, metal-containing glycosides;
   (3) separating the resulting solution from any solid metal-containing byproduct by filtration; and
   (4) promptly following the separation step, rapidly freezing the solution to halt further reaction between glycoside and metal cations.

2. A method according to claim 1 in which n moles of metal cation are employed per mole of glycoside, n being the number of bidentate ligands in the glycoside molecule.

3. A method according to claim 2 wherein the sugar moiety of the glycoside is a daunosaminil group and wherein n is 3.

4. A method according to claim 3 wherein the metal cation is selected from the group consisting of Fe(II), Fe(III), Cu(II) and Co(II).

5. A composition of matter essentially comprising, in monomeric form, a multimetallic chelate of an anthracycline glycoside, the chelated metal being selected from the group consisting of Mn(II), Cd(II), Fe(II), Zn(II), Co(II), pb(II), Ni(II), Al(III), Cu(II), Hg(II), and Fe(III).

6. A composition of matter essentially comprising glycosides of formula:

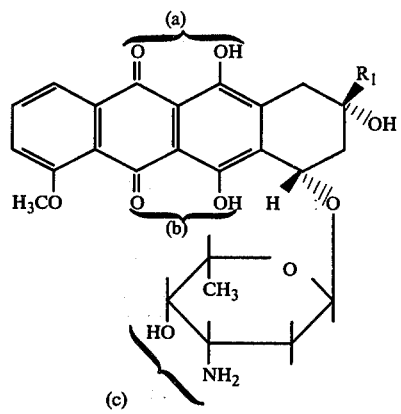

wherein one or more of the bidentate ligands (a), (b) and (c) is occupied by a chelated metal cation selected from the group consisting of Mn(II), Cd(II), Fe(II), Zn(II), Co(II), Pb(II), Ni(II), Al(III), Cu(II), Hg(II), and Fe(III), and wherein R$_1$ is —COCH$_3$ or —COCH$_2$OH, the ratio chelated metal cation to glycoside in the composition being at least about 2.

7. Triferric doxorubicin.

8. Triferric daunorubicin.

9. A pharmaceutical composition comprising an effective amount of at least one essentially monomeric anthracycline glycoside chelate of a metal cation selected from the group consisting of Fe(II), Cu(II), Co(II) and Fe(III) which is ineffective as an inhibitor of Na-K ATPase, in a pharmaceutically acceptable carrier.

10. A method of treating transplanted tumors in mice comprising administering to a tumor-bearing mouse an antitumorally effective amount of a compound selected from the group consisting of triferric doxorubicin and triferric daunorubicin.

* * * * *